United States Patent
Morillo et al.

(10) Patent No.: US 10,258,617 B2
(45) Date of Patent: *Apr. 16, 2019

(54) DOSING REGIMENS FOR FAST ONSET OF ANTIDEPRESSANT EFFECT

(71) Applicant: H. Lundbeck A/S, Valby (DK)

(72) Inventors: Connie Sanchez Morillo, Sudbury, MA (US); Karina Krøjer Søby, Jystrup (DK); Benny Bang-Andersen, Copenhagen S (DK)

(73) Assignee: H. Lundbeck A/S, Valby (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/890,006

(22) Filed: Feb. 6, 2018

(65) Prior Publication Data

US 2018/0153881 A1    Jun. 7, 2018

Related U.S. Application Data

(63) Continuation of application No. 15/703,572, filed on Sep. 13, 2017, now Pat. No. 9,913,839, which is a continuation of application No. 15/636,238, filed on Jun. 28, 2017, now Pat. No. 9,820,984.

(60) Provisional application No. 62/357,722, filed on Jul. 1, 2016.

(51) Int. Cl.
| | |
|---|---|
| *A61K 31/495* | (2006.01) |
| *A61K 9/00* | (2006.01) |
| *A61K 9/08* | (2006.01) |
| *A61K 47/40* | (2006.01) |

(52) U.S. Cl.
CPC .......... *A61K 31/495* (2013.01); *A61K 9/0019* (2013.01); *A61K 9/0053* (2013.01); *A61K 9/08* (2013.01); *A61K 47/40* (2013.01)

(58) Field of Classification Search
CPC .................................................. A61K 31/495
USPC ..................................................... 514/252.1
See application file for complete search history.

(56) References Cited

U.S. PATENT DOCUMENTS

| | | |
|---|---|---|
| 7,144,884 B2 | 12/2006 | Ruhland et al. |
| 8,299,095 B2 | 10/2012 | Bang-Andersen et al. |
| 8,476,279 B2 | 7/2013 | Bang-Andersen et al. |
| 8,507,526 B2 | 8/2013 | Miller |
| 8,598,348 B2 | 12/2013 | Nicolajsen et al. |
| 8,664,225 B2 | 3/2014 | Moore et al. |
| 8,722,684 B2 | 5/2014 | Bang-Andersen et al. |
| 8,940,746 B2 | 1/2015 | Treppendahl et al. |
| 8,969,355 B2 | 3/2015 | Bang-Andersen et al. |
| 9,090,575 B2 | 7/2015 | Ruhland et al. |
| 9,095,588 B2 | 8/2015 | Faldt et al. |
| 9,101,626 B2 | 8/2015 | Faldt et al. |
| 9,125,908 B2 | 9/2015 | Bang-Andersen et al. |
| 9,125,909 B2 | 9/2015 | Bang-Andersen et al. |
| 9,125,910 B2 | 9/2015 | Bang-Andersen et al. |
| 9,133,144 B2 | 9/2015 | Christensen |
| 9,211,288 B2 | 12/2015 | Morillo |
| 9,227,946 B2 | 1/2016 | Faldt et al. |
| 9,278,096 B2 | 3/2016 | Dragheim |
| 9,315,459 B2 | 4/2016 | Bang-Andersen et al. |
| 9,353,073 B2 | 5/2016 | Ruhland et al. |
| 9,475,748 B2 | 10/2016 | Treppendahl et al. |
| 9,820,984 B1 * | 11/2017 | Morillo ................ A61K 31/495 |
| 9,913,839 B2 * | 3/2018 | Morillo ................ A61K 31/495 |
| 2013/0184291 A1 | 7/2013 | Dragheim et al. |
| 2016/0083359 A1 | 3/2016 | Bang-Andersen et al. |
| 2016/0137620 A1 | 5/2016 | Ruhland et al. |
| 2016/0256398 A1 | 9/2016 | Hojer et al. |
| 2016/0368884 A1 | 12/2016 | Lopez de Diego et al. |
| 2017/0037006 A1 | 2/2017 | Bang-Andersen et al. |

FOREIGN PATENT DOCUMENTS

| | | |
|---|---|---|
| WO | WO 03/029232 | 4/2003 |
| WO | WO 2007/144005 | 12/2007 |
| WO | WO 2010/121621 | 10/2010 |
| WO | WO 2014/128207 | 8/2014 |
| WO | WO 2015/091833 | 6/2015 |

OTHER PUBLICATIONS

Areberg, J., et al., "Occupancy of the Serotonin Transporter after Administration of Lu AA21004 and its Relation to Plasma Concentration in Healthy Subjects," Basic & Clin Pharmacol & Tox, 110, 401-404, 2011.
Areberg, J., et al., "Population Pharmacokinetic Meta-Analysis of Vortioxetine in Healthy Individuals," Basic & Clin Pharmacol & Tox, 115, 552-559, 2014.
Areberg, J., et al., "The Clinical Pharmacokinetics of Lu AA21004 and its Major Metabolite in Healthy Young Volunteers," Basic & Clin Pharmacol & Tox, 111, 198-205, 2012.
Bang-Andersen, B., et al., "Discovery of 1-[2-(2,4-Dimethylphenylsulfanyl)phenyl]piperazine (Lu AA21004): A Novel Multimodal Compound for the Treatment of Major Depressive Disorder," J. Med. Chem., 54, 3206-3221, 2011.
Baumann, P., et al., "A double-blind double-dummy study of citalopram comparing infusion versus oral administration," J Affec Dis, 49, 203-210, 1998.
Bitter, C., et al., "Nasal Drug Delivery in Humans," Curr Probl Dermatol, 40, 20-35, 2011.
Blier, P., "Pharmacology of Rapid-Onset Antidepressant Treatment Strategies," J Clin Psych 62 (suppl 15) 12-17, 2001.
Blier, P., "The pharmacology of putative early-onset antidepressant strategies," Eur Neuropsychoparm 13, 57-66, 2003.

(Continued)

*Primary Examiner* — Raymond J Henley, III
(74) *Attorney, Agent, or Firm* — Fish & Richardson P.C.

(57) ABSTRACT

A dose regimes comprising the simultaneous administration of two pharmaceutical compositions, wherein the first pharmaceutical composition is a composition comprising vortioxetine or a pharmaceutically acceptable salt thereof for once daily oral administration, and the second pharmaceutical composition is a composition comprising vortioxetine or a pharmaceutically acceptable salt thereof which together with said first composition quickly achieves a steady-state plasma level of vortioxetine in said patient which steady-state plasma level is the same as the steady-state vortioxetine plasma level achieved by the administration to said patient of said first composition alone.

9 Claims, 1 Drawing Sheet

(56) References Cited

OTHER PUBLICATIONS

Česko-Slovenská et al., "Dosing regimens for fast onset of antidepressant effect" Psychiatrie, 6, 331-339, 1993 with English-language translation.
Dale, E., et al., "Emerging Mechanisms and Treatments for Depression Beyond SSRIs and SNRIs," Biochem Pharmacol, 95, 81-97, 2015.
Davis, S.S., et al., "Absorption Enhancers for Nasal Drug Delivery," Clin Pharmacokinet, 42, 1107-1128, 2003.
Deisenhammer, E.A, et al., "Intravenous Versus Oral Administration of Amitriptyline in Patients with Major Depression," J Clin Psychopharm 20, 417-422, 2000.
Excerpt of slides presented during 2017 ASCP Annual Meeting (Miami Beach, FL, May 29-Jun. 2, 2017) re Montgomery-Asberg Depression Scale (MADRS) (2 pages).
Guelfi, J.D., et al., "Efficacy of Intravenous Citalopram Compared with Oral Citalopram for Severe Depression Safety and Efficacy Data from a Double-Blind, Double-Dummy Trial," J Affect Dis 58, 201-209, 2000.
Häberli, T., "Infusion therapy with antidepressants" Pharma-Kritik, 10, 41-44, 1988 (English Translation).
Laughren, T.P., et al., "Vilazodone: Clinical Basis for the US Food and Drug Administration's Approval of a New Antidepressant" J Clin Psych, 72, 1166-1173, 2011.
McAskill, R., et al., "Pindolol Augmentation of Antidepressant Therapy," Br J Psych 173, 203-208, 1998.
Meyer, J.H., et al., "Occupancy of Serotonin Transporters by Paroxetine and Citalopram During Treatment of Depression: A [11C]DASB PET Imaging Study"Am J Psych 158, 1843-1849, 2001.
Moukaddam, N. J., et al., "Intravenous antidepressants: A review," Depression and Anxiety, vol. 19, No. 1, pp. 1-9 (2004).
Naik, H., et al., "A Population Pharmacokinetic-Pharmacodynamic Meta-Analysis of Vortioxetine in Patients with Major Depressive Disorder," Basic & Clinical Pharmacology & Toxicology, vol. 118, No. 5, pp. 344-355 (2015).
Nord, M., et al., "Effect of a single dose of escitalopram on serotonin concentration in the non-human and human primate brain" Int J Neuropsychpharm 16, 1577-1586, 2013.
O'Leary, O., "Faster, better, stronger: Towards new antidepressant therapeutic strategies" Eur J Pharmacol, 753, 32-50, 2015.
PCT; International Search Report and Written Opinion dated Sep. 13, 2017 in corresponding International application No. PCT/EP2017/065958 (14 pages).
Rosenzweig-Lipson, S., et al., "Differentiating antidepressants of the future: Efficacy and safety" Pharmacol & Ther, 113, 134-153, 2007.
Sanchez, C., et al., "Vortioxetine, a novel antidepressant with multimodal activity: Review of preclinical and clinical data" Pharmacol. & Therap., 145, 43-57, 2015.
Schöny, W., "The efficacy and tolerability of citalopram* in a comparison of parenteral and oral administration" Neuro-psychiatrie, 6, 1-2, pp. 65-71, 1992, with English-language translation.
Selvaraj, S., et al., "Measuring endogenous changes in serotonergic neurotransmission in humans: a [11c]CUMI-101 PET challenge study" Mol Psych 17, 1254-1260, 2012.
Wilner, P., et al., "The neurobiology of depression and antidepressant action," Neurosci Biobehav Rev, 37, 2331-2371, 2013.

* cited by examiner

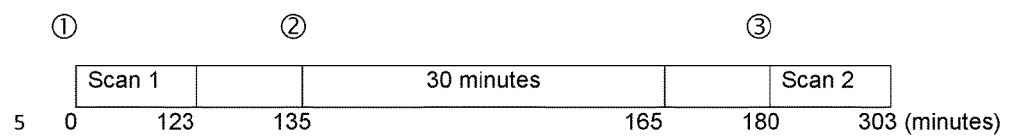

DOSING REGIMENS FOR FAST ONSET OF ANTIDEPRESSANT EFFECT

CROSS REFERENCE TO PRIOR APPLICATIONS

This application is a continuation application of U.S. application Ser. No. 15/703,572, filed Sep. 13, 2017, now U.S. Pat. No. 9,913,839, which is a continuation application of U.S. application Ser. No. 15/636,238, filed Jun. 28, 2017, now U.S. Pat. No. 9,820,984, which claims priority to U.S. Provisional Application Ser. No. 62/357,722, filed Jul. 1, 2016. The prior applications are incorporated by reference herein in their entirety.

FIELD OF THE INVENTION

The present invention relates to a treatment regimen for vortioxetine.

BACKGROUND

The compound 1-[2-(2,4-dimethyl-phenylsulfanyl)-phenyl]piperazine was first disclosed in the International patent application published as WO 03/029232. Later, International patent applications including WO 2007/144005, WO 2011/023194 and WO 2010/121621 have disclosed crystalline forms, manufacturing processes, formulations, and in particular liquid formulations of said compound. World Health Organization (WHO) has recommended the INN name "vortioxetine" for 1-[2-(2,4-dimethyl-phenylsulfanyl)-phenyl]piperazine. Vortioxetine obtained first regulatory approval in September 2013 in the United States of America for the treatment of major depressive disorder and has since then obtained approvals for similar indications throughout the World.

Vortioxetine has multimodal activity, and it has been shown to be an antagonist on the 5-HT3, 5-HT7 and 5-HT1D receptors, an agonist at the 5-HT1A receptor and a partial agonist at the 5-HT1B receptor, and an inhibitor of the serotonin transporter (SERT). 5-HT abbreviates 5-hydroxy tryptamine, i.e. serotonin. Moreover, vortioxetine has demonstrated to increase the levels of important neurotransmitters including serotonin, noradrenaline, dopamine, acetylcholine and histamine in specific areas of the brain [*J. Med. Chem.*, 54, 3206-3221, 2011; *Pharmacol. & Therap.*, 145, 43-57, 2015].

A significant drawback for treatment of depression using oral serotonin reuptake inhibitors is the lag-period between onset of treatment and onset of action which can be many weeks.

Several advantages have been suggested for intravenous (IV) administration of antidepressants compared to oral administration. IV administration avoids first-pass metabolism, and compliance is less of a problem compared to oral administration. In addition, it has been suggested that the IV setting itself may have a favourable impact on the treatment outcome. Finally, and with particular relevance in the present context, some reports in prior art suggest a faster onset of action for IV administration although only a few studies have applied the double-blind/double-dummy study design needed to properly compare onset of action between oral and IV administration of antidepressants.

Häberli in *Pharma-Kritik*, 10, 41-44, 1988 reviews studies comparing clomipramine (tricyclic antidepressant (TCA) with mainly serotonin reuptake inhibitory activity) and maprotilin (tetracyclic antidepressant with mainly noradrenaline reuptake inhibitory activity) in oral and IV administration settings. The conclusion is that antidepressant IV therapy has failed to deliver on the promise of faster onset of action.

Oral and IV administration of amitryptilin (TCA with serotonin and also noradrenaline reuptake inhibitory activity) have been compared in a double-blind/double-dummy study [*J Clin Psychpharm* 20, 417-422, 2000]. No difference in onset of action between the two treatments could be detected.

Oral and IV administration of citalopram (selective serotonin reuptake inhibitor (SSRI)) have been compared in several studies. *Neuropsychiatrie* 6, 65-71, 1992 reports on an open-label study where depressed patients received repeated oral (N=475) or IV citalopram (N=284) for 10-14 days followed by 4-6 weeks of oral treatment. An earlier onset of action in the IV treated group was observed although it also has to be noticed that the mean dose during the first 10-14 days for the IV treated patients was twice that of the dose for the orally treated patients. More than 50% of the participating doctors with patients on initial IV treatment indicated that an expectation of faster onset was the main reason for administering IV treatment to their patients.

Česko-Slovenská Psychiatrie, 6, 331-339, 1993 reports on a study where 101 depressed patients were enrolled in an open-label study to receive either 28 days oral citalopram or 14 days IV citalopram followed by 14 days oral citalopram. A significantly faster onset of action was observed in the IV treated group.

*J Affec Dis*, 49, 203-210, 1998 reports on a double-blind, double-dummy study comparing oral and IV administration of citalopram. 60 depressed patients were treated with either repeated citalopram tablets and placebo IV or repeated citalopram IV and placebo tablets for 10 days followed by oral citalopram for additional 32 days. No statistical difference in onset of action could be detected between the two groups for any efficacy parameter although a tendency toward a quicker onset of action was seen when measured as percentage of patients with more than 50% reduction of the score on the Hamilton Depression Scale compared to baseline.

*J Affect Dis* 58, 201-209, 2000 reports on a further double-blind, double-dummy study comparing oral and IV administration of citalopram. Depressed patients were randomised to repeated citalopram tablets and placebo IV (N=119) or repeated citalopram IV and placebo tablets (N=135) for 8 days followed by 34 days of oral citalopram treatment. No difference in the Montgomery-Åsberg Depression Rating Scale (MADRS) at day 8 was found, which was the primary efficacy end-point. However, improvements on the Global Clinical Impression scale at day 8 were observed for more patients in the IV arm than in the oral arm.

In conclusion, past well-controlled studies have generally failed to show a faster onset of action for antidepressants, and in particular for antidepressant with serotonin reuptake inhibitory effect, administered via the IV route compared to oral administration.

*Basic & Clin Pharmacol & Tox*, 111, 198-205, 2012 discloses a series of studies to define the clinical pharmacokinetics of vortioxetine. One of the studies was a single-dose, open-label, 2-way crossover study where healthy volunteers received oral and IV vortioxetine with a wash-out period of at least 18 days between the two administrations.

One aim of the present invention is to provide a treatment regime for vortioxetine which achieves a faster onset of action compared to orally administered vortioxetine.

SUMMARY OF THE INVENTION

The present inventors have surprisingly found that vortioxetine, contrary to what is found for SSRI's, gives rise to a large increase in serotonin concentrations in parts of the brain relevant for mood upon acute administration. Such increase in serotonin concentration is indicative of a fast or immediate onset of antidepressant action. Accordingly, in one embodiment, the invention provides a method for the treatment of depression, said method comprising the simultaneous administration of two pharmaceutical compositions to a patient in need thereof, wherein the first pharmaceutical composition is a composition comprising vortioxetine or a pharmaceutically acceptable salt thereof for once daily oral administration, and the second pharmaceutical composition is a composition comprising vortioxetine or a pharmaceutically acceptable salt thereof which together with said first composition achieves a steady-state plasma level of vortioxetine in said patient within 36 hours from said simultaneous administration which steady-state plasma level is essentially the same as the steady-state vortioxetine plasma level achieved by the administration to said patient of said first composition alone.

In one embodiment, the invention relates to an oral pharmaceutical composition comprising vortioxetine or a pharmaceutically acceptable salt thereof for once daily oral administration for use in the treatment of depression wherein said oral pharmaceutical composition is simultaneously administered to a patient in need thereof with a pharmaceutical composition comprising vortioxetine or a pharmaceutically acceptable salt thereof and wherein said simultaneous administration achieves a steady-state vortioxetine plasma level within 36 hours from said simultaneous administration in said patient which steady-state vortioxetine plasma level is essentially the same as the steady-state vortioxetine plasma level achieved by the administration to said patient of said oral pharmaceutical composition alone.

In one embodiment, the invention relates to a pharmaceutical composition comprising vortioxetine or a pharmaceutically acceptable salt thereof for use in the treatment of depression wherein said pharmaceutical composition is simultaneously administered to a patient in need thereof with an oral pharmaceutical composition comprising vortioxetine or a pharmaceutically acceptable salt thereof for once daily administration wherein said simultaneous administration achieves a steady-state vortioxetine plasma level within 36 hours from said simultaneous administration in said patient which steady-state vortioxetine plasma level is essentially the same as the steady-state vortioxetine plasma level achieved by the administration to said patient of said oral pharmaceutical composition alone.

In one embodiment, the invention relates to two pharmaceutical compositions for use in a method for the treatment of depression which compositions are simultaneously administered to a patient in need thereof, wherein the first pharmaceutical composition is a composition comprising vortioxetine or a pharmaceutically acceptable salt thereof for once daily oral administration and the second pharmaceutical composition is a composition comprising vortioxetine or a pharmaceutically acceptable salt thereof which together with said first composition achieves a steady-state plasma level of vortioxetine in said patient within 36 hours from said simultaneous administration which steady-state vortioxetine plasma level is essentially the same as the steady-state vortioxetine plasma level achieved by the administration to said patient of said first composition alone.

In one embodiment, the invention relates to the use of vortioxetine or a pharmaceutically acceptable salt thereof in the manufacture of a first pharmaceutical composition for once daily oral administration for the treatment of depression, wherein said first pharmaceutical composition is administered to a patient simultaneous with a second pharmaceutical composition comprising vortioxetine or a pharmaceutically acceptable salt thereof and wherein said simultaneous administration achieves a steady-state vortioxetine plasma level within 36 hours from said simultaneous administration in said patient which steady-state vortioxetine plasma level is essentially the same as the steady-state vortioxetine plasma level achieved by the administration to said patient of said first composition alone.

In one embodiment, the invention relates to the use of vortioxetine or a pharmaceutically acceptable salt thereof in the manufacture of a pharmaceutical composition for the treatment of depression, wherein said pharmaceutical composition is administered to a patient simultaneous with a once daily oral pharmaceutical composition comprising vortioxetine or a pharmaceutically acceptable salt thereof and wherein said simultaneous administration achieves a steady-state vortioxetine plasma level in said patient within 36 hours from said simultaneous administration which steady-state vortioxetine plasma level is essentially the same as the steady-state vortioxetine level achieved by administration of said oral pharmaceutical composition to said patient alone.

BRIEF DESCRIPTION OF DRAWING

FIG. 1: The study design used for the PET studies in Example 1. ① Administration of [$^{11}$C]AZ10419369 or [$^{11}$C]MADAM; ② administration of vortioxetine 0.3 mg/kg IV, vortioxetine 1 mg/kg IV, or citalopram 0.3 mg/kg IV; ③ Administration of [$^{11}$C]AZ10419369 or [$^{11}$C]MADAM.

DETAILED DESCRIPTION OF THE INVENTION

The present invention relates to vortioxetine or a pharmaceutically acceptable salt thereof. Vortioxetine is commercially available or can be synthesised as disclosed in e.g. WO 03/029232, WO 2007/144005 or WO 2014/128207. The molecular structure of vortioxetine is depicted below.

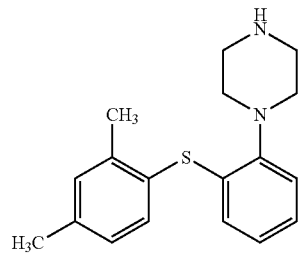 [SMILES: Cc1ccc(Sc2ccccc2N2CCNCC2)c(C)c1]

In the present context, "pharmaceutically acceptable salt" is intended to indicate a salt formed in the reaction between vortioxetine and a non-toxic acid. Examples of such acid include hydrochloride acid, hydrobromide acid, phosphoric acid, nitrous acid, sulphuric acid, benzoic acid, citric acid, gluconic acid, lactic acid, maleic acid, succinic acid, tartaric acid, acetic acid, propionic acid, oxalic acid, maleic acid, glutamic acid, pyroglutamic acid, salicylic acid, salicylic acid and sulfonic acids, such as ethanesulfonic acid, toluenesulfonic acid and benzenesulfonic acid. Specific mention is made of the HBr and the DL-lactic acid salts. Additional examples of useful acids to form pharmaceutically acceptable salts can be found e.g. in Stahl and Wermuth (Eds) "Handbook of Pharmaceutical salts. Properties, selection, and use", Wiley-VCH, 2008.

Any indication of an amount or concentration of vortioxetine or a pharmaceutically acceptable salt thereof is intended to indicate such amount or concentration as the free base, unless otherwise specifically indicated. The molecular weight of vortioxetine HBr is 379.4 g/mol and that of vortioxetine is 298.5 g/mol. Therefore, a composition comprising vortioxetine HBr indicated to comprise 20 mg vortioxetine actually comprises 25.4 mg vortioxetine HBr.

Depression is a mental state characterised by, e.g., depressed mood and a feeling of sadness, emptiness, helplessness or worthlessness. As a psychiatric syndrome depression includes depressive disorders, e.g., as defined in DSM-V. Depressive disorders include disruptive mood dysregulation disorder, major depressive disorder, persistent depressive disorder and premenstrual dysphoric disorder. In one embodiment, "depression" is intended to indicate major depressive disorder.

Treatment of depression using serotonin reuptake inhibitors is often characterised by a delay between the treatment start and the onset of therapeutic action. This delay is typically measured in weeks, and the delay is critical for several reasons including the fact that remission is more likely to be achieved in patients with a fast treatment response. Obviously, a patient would normally also wish for a fast resolution of symptoms related to any disease, including depression. It may also be noted that patients may only experience the adverse events associated with the antidepressant treatment in that period without the benefit of a therapeutic effect. Therefore, there is a risk that patients may stop taking the antidepressant with the consequent reduced likelihood of a successful treatment. Moreover, the lag-time between onset of treatment and onset of action has been associated with an increased risk of suicide [*Eur Neuropsychoparm* 13, 57-66, 2003].

The latency of onset of clinical effect from antidepressant treatment, including treatment with serotonin reuptake inhibitors, has been recognised as a major limitation since the advent of these drugs. That this limitation still exists is evidenced by two review articles spanning the last decade—see *Pharmacol & Ther,* 113, 134-153, 2007 and *Eur J Pharmacol,* 753, 32-50, 2015.

Serotonin is a neurotransmitter passing nerve signals between nerve cells (neurons) over the synaptic cleft. A presynaptic (or signal-passing) neuron releases serotonin into the synaptic space in response to electrical activity in said cell. Here, serotonin interacts with receptors in the membrane of a post-synaptic (or signal-receiving) neuron and thereby passes the nerve signal from one cell to the other. To maintain this mechanism, serotonin is subsequently reabsorbed into the neurons via the serotonin transporter which is a protein complex located in the cell membrane of the neuron. According to the monoamine theory for depression, depression is associated with inadequate nerve signalling in parts of the brain, and the effect of serotonin transport inhibitors may be explained by a blocking of the serotonin transporter (i.e., the serotonin reuptake) thereby causing an increase of serotonin in the synaptic cleft and a normalization of nerve signalling.

The delay of onset of action has been explained by several factors including activation of serotonin receptors, and in particular the serotonin receptor 1A ($5\text{-HT}_{1A}$). The increase in synaptic serotonin level as a consequence of the inhibition of serotonin reuptake stimulates $5\text{-HT}_{1A}$ receptors which are part of a feedback inhibitory system bringing about a lower release of serotonin from the pre-synaptic neurons. Over time (several weeks), the $5\text{-HT}_{1A}$ receptors are desensitized, the feedback inhibitory system inactivated and the serotonin release normalised which together with the inhibition of serotonin reuptake eventually causes an increase in serotonin in the synapse [*J Clin Psych* 62 (suppl 15) 12-17, 2001].

In clinical practice, treatment with antidepressants is normally continued for a considerable amount of time after a successful resolution of the symptoms of depression has been achieved in order to minimize the risk of relapse [The Maudsley Prescribing Guidelines, $9^{th}$ Edition, Informa Healthcare, 2008].

It has been suggested that adding a $5\text{-HT}_{1A}$ receptor partial agonist or antagonists, such as pindolol, to an SSRI treatment could give rise to a blocking or faster desensitization of the $5\text{-HT}_{1A}$ receptors and therefore a faster onset of action and/or an augmentation of the antidepressant effect. It has also been suggested that the combination of a serotonin reuptake inhibitor with compounds acting on various other serotonin receptors, such as $5\text{-HT}_{2A}$ and $5\text{-HT}_{2C}$ receptor antagonists provides a faster increase in serotonin in the synaptic cleft implying a faster onset of action or increased effect [*Biochem Pharmacol,* 95, 81-97, 2015]. However, clinical investigations of pindolol as add-on to antidepressants have delivered mixed results with open label studies often favouring the combination but with lack of support to these findings from controlled studies [*Br J Psych* 173, 203-208, 1998].

Recently approved antidepressants with a pharmacological profile which could hold a promise of a faster onset of action have not successfully shown a shorter period of time between onset of treatment and onset of action. Vilazodone is a serotonin reuptake inhibitor and $5\text{-HT}_{1A}$ receptor partial agonist approved by FDA for the treatment of depression in 2011. Despite early reports of faster onset of action, the pivotal studies did not support such claim [*J Clin Psych,* 72, 1166-1173, 2011]. More recently, FDA approved vortioxetine which, as discussed above, is a multimodal compound with a pharmacological profile which includes serotonin reuptake inhibition and $5\text{-HT}_{1A}$ receptor agonism. However, according to the FDA label for vortioxetine of July 2014 an effect of vortioxetine is observed starting at week 2 and with the full antidepressant effect of the drug not seen until week 4.

More recently, alternatives to augmented SSRI treatment have been suggested as ways to achieve a faster onset of antidepressant effect. Wilner et al in *Neurosci Biobehav Rev,* 37, 2331-2371, 2013 suggest deep brain stimulation (DBS) which is a neurosurgical treatment where an electrode, which sends electrical impulses, is implanted in the brain as a way to achieve fast onset of effect. Similarly, electroconvulsive therapy (ECT), intravenous administration of ketamine and REM-sleep deprivation are suggested as fast onset antidepressant techniques.

As discussed above, and according to the monoamine theory, depression is a disorder caused by low serotonergic activity, and treatment with e.g., serotonin reuptake inhibitors is intended to induce an increase in serotonin level in the brain which will normalize this activity and thereby treat the disease. A faster increase in the serotonin level in relevant parts of the brain would be expected to be associated with a faster onset of treatment effect.

Positron emission tomography (PET) is an imaging technique which allows the measurement of the level of radio nucleotides (as part of the PET ligand) introduced into the body. The recent advent of a PET ligand which specifically binds to the 5-HT$_{1B}$ receptor, [$^{11}$C]AZ10419369, has made possible the use of PET scanners to non-invasively determine alterations in serotonin level in specific areas of the brain relevant for mood [Int J Neuropsychpharm 16, 1577-1586, 2013]. The chemical name for [$^{11}$C]AZ10419369 is 5-methyl-8-(4-[$^{11}$C]methyl-piperazin-1-yl)-4-oxo-4H-chromene-2-carboxylic acid (4-morpholin-4-yl-phenyl)-amide. In summary, the PET ligand binds specifically to the 5-HT$_{1B}$ receptor and is displaced by the endogenous ligand, serotonin, if the level of serotonin increases. Thus, a decrease in the PET ligand-5-HT$_{1B}$ receptor specific binding (measured as binding potential, BP$_{ND}$) upon administration of a drug is taken to indicate an increase in the serotonin level in that particular part of the brain. Conversely, an increase in BP$_{ND}$ is taken to indicate a decrease in serotonin level.

The central serotonergic system in the brain originates in the raphe nuclei (RN) which is divided into several subgroups with, in particular, the dorsal raphe nucleus (DRN) projecting into the cortical and striatal areas of the brain. Using PET scanning with [$^{11}$C]AZ10419369 as ligand changes in relevant parts of the brain of monkeys upon acute administration of the SSRI escitalopram (2.0 mg/kg) have been determined. The parts in the brain investigated included the dorsolateral prefrontal cortex (DLPFC), the occipital cortex (OC), the caudate nucleus (CN), the putamen (Put), the thalamus (Thal), the globus pallidus (GP) the midbrain (MB), the hippocampus and the cerebellum (CB) [Int J Neuropsychpharm 16, 1577-1586, 2013]. The table below shows the changes in BP$_{ND}$ in the various brain regions.

| Region | ΔBP$_{ND}$ (% of baseline) | p value |
| --- | --- | --- |
| DLPFC | −12 ± 12 | 0.03 |
| OC | 12 ± 10 | 0.02 |
| CN | −9 ± 14 | 0.1 |
| Put | −11 ± 14 | 0.1 |
| Thal | −13 ± 8 | 0.005 |
| GP | −7 ± 10 | 0.08 |
| MB | −11 ± 10 | 0.03 |
| HC | −12 ± 14 | 0.07 |
| RN | −25 ± 16 | 0.002 |

Similarly, the change in BP$_{ND}$ upon acute administration of escitalopram (20 mg per oral) in humans (healthy volunteers) was determined with the result indicated in the table below. Additional projections in the brain investigated were the frontal cortex (FC) and the temporal cortex (TC).

| Region | ΔBP$_{ND}$ (% of baseline) | p value |
| --- | --- | --- |
| FC | 6 ± 7 | 0.05 |
| OC | 5 ± 5 | 0.01 |
| TC | 5 ± 6 | 0.04 |
| CN | 6 ± 10 | 0.1 |
| Put | 5 ± 8 | 0.08 |
| Thal | 6 ± 13 | 0.2 |
| RN | −9 ± 13 | 0.08 |
| Cortical regions | 5 ± 5 | 0.01 |
| Subcortical regions | 6 ± 8 | 0.07 |
| All projection areas | 5 ± 5 | 0.01 |

Overall, the change in BP$_{ND}$ in both human and monkey is relatively small in most projections of the brain and often not significant. The results from the monkey studies seem to suggest a small and not always significant decrease in BP$_{ND}$, i.e. an increase in serotonin level upon escitalopram administration. However, it has to be kept in mind that the dose administered to the monkey gave a plasma level which was approximately 7 times that found in humans after administration of a therapeutically relevant dose. The results from the human studies seem to indicate a small increase in BP$_{ND}$, i.e. a decrease in serotonin level upon escitalopram administration. Escitalopram was dosed in a therapeutically relevant amount. The only projection in which an increase in serotonin level was indicated was RN, and this increase did not reach significance.

A similar study has been conducted in humans to measure the effect on serotonin levels in the brain upon acute administration of the SSRI citalopram [Mol Psych 17, 1254-1260, 2012]. This study used [$^{11}$C]CUMI which is a 5-HT$_{1A}$ receptor specific PET ligand. The changes in BP$_{ND}$ shown below indicate a modest increase in serotonin level in DR and a modest decrease in serotonin level in FC, HC and OC of which only the decrease in FC reached significance.

| Region | ΔBP$_{ND}$ (% of baseline) | p value |
| --- | --- | --- |
| FC | 6.5 | 0.006 |
| HC | 5.5 | 0.56 |
| OC | 2.9 | 0.18 |
| DR | −2.7 | 0.03 |

The above discussed experimental observations for citalopram and escitalopram are in line with the clinical experience with these compounds, i.e. that a lag-time normally exists between the initiation of treatment and an observation of a clinical effect.

The study reported in Example 1 is similar to those discussed above and compares the change in BP$_{ND}$, i.e. the change in serotonin in relevant parts of the brain following administration of clinically relevant doses of vortioxetine and citalopram to monkeys.

Vortioxetine was tested at two different dose levels (0.3 mg/kg and 1.0 mg/kg) which levels span the SERT occupancy reached at clinically relevant doses. Citalopram was tested at a single dose level (0.3 mg/kg) which was also shown to result in a clinically relevant SERT occupancy. Vortioxetine at both doses produced a much larger reduction in BP$_{ND}$, i.e. an increase in serotonin, compared to citalopram, and also compared to what has previously been observed with escitalopram and citalopram. In fact, citalopram in the present study in all but one projection area gives rise to a decrease in serotonin level. For vortioxetine at the high dose the increase in serotonin reaches significance in all projection areas investigated. This shows that vortioxetine, contrary to other serotonin reuptake inhibitors investigated, gives rise to a large (and dose dependent) increase in serotonin upon acute IV administration.

From this observation, it is concluded that vortioxetine administered in a way that ensures clinically relevant plasma levels are achieved fast and subsequently maintained will result in a fast onset of action.

A fast increase in plasma level of vortioxetine may be achieved in several ways that avoids absorption through the intestines including IV administration, nasal administration, rectal administration buccal administration and sublingual administration. In particular IV administration but also nasal and rectal administration may be inconvenient to the patient as part of a long-term treatment, that is a treatment with the aim to maintain a therapeutically relevant vortioxetine plasma level for weeks, months or even years. These administration forms may therefore conveniently be combined with other administration forms, e.g. oral administration in a way so that a clinically relevant plasma level is initially achieved fast using simultaneous administration as disclosed herein and wherein said plasma level is subsequently maintained using oral administration.

The above fast onset hypothesis was tested in a clinical trial reported in Example 3. Patients treated with placebo IV on day 0 and oral vortioxetine on day 0 to day 14 were compared to patients treated with vortioxetine IV on day 0 and oral vortioxetine on day 0 to day 14 in a double-blind/double dummy study. The results show a marked response to both treatment arms. Moreover, the results show that early in the study (day 1-7) patients in the vortioxetine IV arm experience a faster and larger response compared to the patients in the placebo IV arm. Later in the study, i.e. at day 14 the difference between the two arms disappears. That the responses in the two treatment arms converge late in the study is expected because the effects of the IV administration early in the study (day 0) eventually will fade. The results from this clinical study confirm the fast on-set hypothesis build on the PET monkey data, namely that a vortioxetine dosing regimen that results in a fast increase in the vortioxetine plasma level to steady-state level (for standard oral treatment) provides a faster onset of an anti-depressant effect. More specifically, the result in Example 3 show that a once daily oral dose of vortioxetine of a pharmaceutically acceptable salt thereof administered simultaneously with a second pharmaceutical composition comprising vortioxetine of a pharmaceutically acceptable salts thereof (e.g. single IV dose) where the combined administration achieves a steady-state plasma level of vortioxetine fast which steady-state level is essentially the same as the vortioxetine plasma steady-state level achieved by the administration of once-daily oral vortioxetine alone will result in fast onset of an anti-depressive effect. The results obtained in Example 3 show that a combination of a single IV dose of vortioxetine followed by oral administration of vortioxetine gives rise to a faster and larger anti-depressant effect than what has previously been experienced with other antidepressants, i.e. citalopram in similar settings—see *J Affect Dis,* 49, 203-210, 1998 and *J Affect Dis,* 58, 201-209, 2000.

In one embodiment, the invention provides a method for the treatment of depression, said method comprising the simultaneous administration of two pharmaceutical compositions to a patient in need thereof, wherein the first pharmaceutical composition is a composition comprising vortioxetine or a pharmaceutically acceptable salt thereof for once daily oral administration, and the second pharmaceutical composition is a composition comprising vortioxetine or a pharmaceutically acceptable salt thereof which together with said first composition achieves a steady-state plasma level of vortioxetine in said patient within 36 hours from said simultaneous administration which steady-state plasma level is essentially the same as the steady-state vortioxetine plasma level achieved by the administration to said patient of said first composition alone. In one embodiment, the administration of said second composition takes places a limited number of times, such as 1, 2 or 3 times, such as 1 time.

In one embodiment, the invention relates to an oral pharmaceutical composition comprising vortioxetine or a pharmaceutically acceptable salt thereof for once daily oral administration for use in the treatment of depression wherein said oral pharmaceutical composition is simultaneously administered to a patient in need thereof with a pharmaceutical composition comprising vortioxetine or a pharmaceutically acceptable salt thereof and wherein said simultaneous administration achieves a steady-state vortioxetine plasma level within 36 hours from said simultaneous administration in said patient which steady-state vortioxetine plasma level is essentially the same as the steady-state vortioxetine plasma level achieved by the administration to said patient of said oral pharmaceutical composition alone. In one embodiment, the administration of said pharmaceutical composition takes places a limited number of times, such as 1, 2 or 3 times, such as 1 time.

In one embodiment, the invention relates to a pharmaceutical composition comprising vortioxetine or a pharmaceutically acceptable salt thereof for use in the treatment of depression wherein said pharmaceutical composition is simultaneously administered to a patient in need thereof with an oral pharmaceutical composition comprising vortioxetine or a pharmaceutically acceptable salt thereof for once daily administration wherein said simultaneous administration achieves a steady-state vortioxetine plasma level within 36 hours from said simultaneous administration in said patient which steady-state vortioxetine plasma level is essentially the same as the steady-state vortioxetine plasma level achieved by the administration to said patient of said oral pharmaceutical composition alone. In one embodiment, the administration of said pharmaceutical composition takes places a limited number of times, such as 1, 2 or 3 times, such as 1 time.

In one embodiment, the invention relates to two pharmaceutical compositions for use in a method for the treatment of depression which compositions are simultaneously administered to a patient in need thereof, wherein the first pharmaceutical composition is a composition comprising vortioxetine or a pharmaceutically acceptable salt thereof for once daily oral administration and the second pharmaceutical composition is a composition comprising vortioxetine or a pharmaceutically acceptable salt thereof which together with said first composition achieves a steady-state plasma level of vortioxetine in said patient within 36 hours from said simultaneous administration which steady-state vortioxetine plasma level is essentially the same as the steady-state vortioxetine plasma level achieved by the administration to said patient of said first composition alone. In one embodiment, the administration of said second composition takes places a limited number of times, such as 1, 2 or 3 times, such as 1 time.

In one embodiment, the invention relates to the use of vortioxetine or a pharmaceutically acceptable salt thereof in the manufacture of a first pharmaceutical composition for once daily oral administration for the treatment of depression, wherein said first pharmaceutical composition is administered to a patient simultaneous with a second pharmaceutical composition comprising vortioxetine or a pharmaceutically acceptable salt thereof and wherein said simultaneous administration achieves a steady-state vortioxetine plasma level within 36 hours from said simultaneous administration in said patient which steady-state vortioxetine plasma level is essentially the same as the steady-state vortioxetine plasma level achieved by the administration to said patient of said first composition alone. In one embodiment, the administration of said second composition takes places a limited number of times, such as 1, 2 or 3 times, such as 1 time.

In one embodiment, the invention relates to the use of vortioxetine or a pharmaceutically acceptable salt thereof in the manufacture of a pharmaceutical composition for the treatment of depression, wherein said pharmaceutical composition is administered to a patient simultaneously with a once daily oral pharmaceutical composition comprising vortioxetine or a pharmaceutically acceptable salt thereof and wherein said simultaneous administration achieves a steady-state vortioxetine plasma level in said patient within 36 hours from said simultaneous administration which steady-state vortioxetine plasma level is essentially the same as the steady-state vortioxetine level achieved by administration of said oral pharmaceutical composition to said patient alone. In one embodiment, the administration of said pharmaceutical composition takes places a limited number of times, such as 1, 2 or 3 times, such as 1 time.

In one embodiment, the invention relates to a kit comprising a first pharmaceutical composition which is a composition for once daily oral administration comprising vortioxetine or a pharmaceutically acceptable salt thereof and a second pharmaceutical composition which second pharmaceutical composition is a composition comprising vortioxetine or a pharmaceutically acceptable salt thereof, which second composition when administered to a patient simultaneously with said first composition achieves a steady-state plasma level of vortioxetine in said patient within 36 hours from said simultaneous administration which steady-state vortioxetine plasma level is essentially the same as the steady-state vortioxetine plasma level achieved by the administration to said patient of said first composition alone.

In one embodiment, "simultaneous" or "simultaneously" is intended to indicate that the initiation of the administration of the two compositions is initiated essentially at the same time such as at the same day, such as within 8 hours, such as within 6 hours, such as within 2 hours of each other.

Whereas the composition for oral administration of the present invention is intended for continued or long-term treatment, the second composition of the present invention is only administered a few times, such as 1, 2 or 3 times at the start of the treatment.

Upon multiple oral administration of a drug, such as vortioxetine, the drug is absorbed from the intestines at a certain rate and once in the blood (or plasma) eliminated though metabolic processes. In the present context, "steady-state plasma level" is intended to indicate the plasma level at a point in time (after multiple administrations) where the drug absorption is in equilibrium with drug elimination. Because plasma drug concentrations fluctuate (also at steady-state), the steady-state plasma level is conveniently stated as the plasma concentration integrated over time, also referred to as area under the curve (AUC). For a drug, such as vortioxetine with once daily oral administration, AUC for a 24 hour period ($AUC_{0-24}$) is conveniently used.

The steady-state plasma level of vortioxetine upon once daily oral administration of 5 mg, 10 mg, 15 mg and 20 mg vortioxetine is found to be 161 ng h/ml, 323 ng h/ml, 484 ng h/ml and 645 ng h/ml, respectively (median $AUC_{0-24}$). In addition, the following 95% prediction intervals were calculated: 68; 406 ng h/ml for 5 mg/day; 137; 812 ng h/ml for 10 mg/day; 205; 1219 ng h/ml for 15 mg/day; and 273; 1625 ng h/ml for 20 mg/day. [*Basic & Clin Pharmacol & Tox*, 115, 552-559, 2014]. With once daily oral vortioxetine administration steady-state plasma concentration of vortioxetine is achieved after approximately 8 days [*Basic & Clin Pharmacol & Tox*, 111, 198, 205, 2012].

An element of the present invention is the simultaneous administration of two pharmaceutical compositions to a patient in need thereof, wherein the first pharmaceutical composition is a composition comprising vortioxetine or a pharmaceutically acceptable salt thereof for once daily oral administration, and the second pharmaceutical composition is a composition comprising vortioxetine or a pharmaceutically acceptable salt thereof aiming at achieving a steady-state plasma level of vortioxetine in said patient within 36 hours from said simultaneous administration which steady-state plasma level is essentially the same as the steady-state vortioxetine plasma level achieved by the administration to said patient of said first composition alone. In one embodiment, said steady-state level is achieved within 24 hours from said simultaneous administration, such as with 18 hours, such as within 12 hours.

In one embodiment, the oral composition of the present invention comprising vortioxetine or a pharmaceutically acceptable salt thereof comprises 5 mg-20 mg vortioxetine, such as 5 mg, 10 mg, 15 mg or 20 mg vortioxetine.

In one embodiment, the invention provides a method for the treatment of depression, said method comprising the simultaneous administration of two pharmaceutical compositions to a patient in need thereof, wherein the first pharmaceutical composition is a composition comprising 5 mg-20 mg vortioxetine or a pharmaceutically acceptable salt thereof for once daily oral administration, and the second pharmaceutical composition is a composition comprising vortioxetine or a pharmaceutically acceptable salt thereof which together with said first composition achieves a steady-state plasma level of vortioxetine in said patient within 36 hours, such as within 24 or 18 or 12 hours from said simultaneous administration between 68 ng h/ml and 1625 ng h/ml, such as between 150 ng h/ml and 700 ng h/ml ($AUC_{0-24}$). In one embodiment, said first pharmaceutical composition comprises 5 mg vortioxetine or a pharmaceutically acceptable salt thereof and the steady-state vortioxetine plasma level is between 68 ng h/ml and 406 ng h/ml, such as between 150 ng h/ml and 170 ng h/ml, such as between 155 ng h/ml and 165 ng h/ml. In one embodiment, said first pharmaceutical composition comprises 10 mg vortioxetine or a pharmaceutically acceptable salt thereof and the steady-state vortioxetine plasma level is between 137 ng h/ml and 812 ng h/ml, such as between 145 ng ml/h and 315 ng h/ml, such as between 200 ng h/ml and 300 ng h/ml or between 300 ng h/ml and 340 ng h/ml, such as between 310 ng h/ml and 330 ng h/ml. In one embodiment, said first pharmaceutical composition comprises 15 mg vortioxetine or a pharmaceutically acceptable salt thereof and the steady-state vortioxetine plasma level is between 205 ng h/ml and 1219 ng h/ml, such as between 460 ng h/ml and 510 ng h/ml, such as between 470 ng h/ml and 500 ng h/ml. In one embodiment, said first pharmaceutical composition comprises 20 mg vortioxetine or a pharmaceutically acceptable salt thereof and the steady-state vortioxetine plasma level is between 273 ng h/ml and 1625 ng h/ml, such as between 600 ng h/ml and 700 ng h/ml, such as between 630 ng h/ml and 660 ng h/ml.

In one embodiment, the invention relates to an oral pharmaceutical composition comprising 5 mg-20 mg vortioxetine or a pharmaceutically acceptable salt thereof for once daily oral administration for use in the treatment of depression wherein said oral pharmaceutical composition is simultaneously administered to a patient in need thereof with a pharmaceutical composition comprising vortioxetine or a pharmaceutically acceptable salt thereof and wherein said simultaneous administration achieves a steady-state vortioxetine plasma level within 36 hours, such as within 24 or 18 or 12 hours from said simultaneous administration in said patient between 68 ng h/ml and 1625 ng h/ml, such as between 150 ng h/ml and 700 ng h/ml ($AUC_{0-24}$). In one embodiment, said oral pharmaceutical composition comprises 5 mg vortioxetine or a pharmaceutically acceptable salt thereof and the steady-state vortioxetine plasma level is between 68 ng h/ml and 406 ng h/ml, such as between 150 ng h/ml and 170 ng h/ml, such as between 155 ng h/ml and 165 ng h/ml. In one embodiment, said oral pharmaceutical composition comprises 10 mg vortioxetine or a pharmaceutically acceptable salt thereof and the steady-state vortioxetine plasma level is between 137 ng h/ml and 812 ng h/ml, such as between 145 ng h/ml and 315 ng h/ml ng h/ml, such as between 200 ng h/ml and 300 ng h/ml or between 300 ng h/ml and 340 ng h/ml, such as between 310 ng h/ml and 330 ng h/ml. In one embodiment, said oral pharmaceutical composition comprises 15 mg vortioxetine or a pharmaceutically acceptable salt thereof and the steady-state vortioxetine plasma level is between 295 ng h/ml and 1219 ng h/ml, such as between 460 ng h/ml and 510 ng h/ml, such as between 470 ng h/ml and 500 ng h/ml. In one embodiment, said oral pharmaceutical composition comprises 20 mg vortioxetine or a pharmaceutically acceptable salt thereof and the steady-state vortioxetine plasma level is between 273 ng h/ml and 1625 ng h/ml, such as between 600 ng h/ml and 700 ng h/ml, such as between 630 ng h/ml and 660 ng h/ml.

In one embodiment, the invention relates to a pharmaceutical composition comprising vortioxetine or a pharmaceutically acceptable salt thereof for use in the treatment of depression wherein said pharmaceutical composition is simultaneously administered to a patient in need thereof with an oral pharmaceutical composition comprising 5 mg-20 mg vortioxetine or a pharmaceutically acceptable salt thereof for once daily administration wherein said simultaneous administration achieves a steady-state vortioxetine plasma level within 36 hours, such as within 24 or 18 or 12 hours from said simultaneous administration in said patient which steady-state vortioxetine plasma level between 68 ng h/ml and 1625 ng h/ml, such as between 150 ng h/ml and 700 ng h/ml ($AUC_{0-24}$). In one embodiment, said oral pharmaceutical composition comprises 5 mg vortioxetine or a pharmaceutically acceptable salt thereof and the steady-state vortioxetine plasma level is between 68 ng h/ml and 406 ng h/ml, such as between 150 ng h/ml and 170 ng h/ml, such as between 155 ng h/ml and 165 ng h/ml. In one embodiment, said oral pharmaceutical composition comprises 10 mg vortioxetine or a pharmaceutically acceptable salt thereof and the steady-state vortioxetine plasma level is between 137 ng h/ml and 812 ng h/ml, such as between 145 ng h/ml and 315 ng h/ml, such as between 200 ng h/ml and 300 ng h/ml, or between 300 ng h/ml and 340 ng h/ml, such as between 310 ng h/ml and 330 ng h/ml. In one embodiment, said oral pharmaceutical composition comprises 15 mg vortioxetine or a pharmaceutically acceptable salt thereof and the steady-state vortioxetine plasma level is between 205 ng h/ml and 1219 ng h/ml, such as between 460 ng h/ml and 510 ng h/ml, such as between 470 ng h/ml and 500 ng h/ml. In one embodiment, said oral pharmaceutical composition comprises 20 mg vortioxetine or a pharmaceutically acceptable salt thereof and the steady-state vortioxetine plasma level is between 273 ng h/ml and 1625 ng h/ml, such as between 600 ng h/ml and 700 ng h/ml, such as between 630 ng h/ml and 660 ng h/ml.

In one embodiment, the invention relates to two pharmaceutical compositions for use in a method for the treatment of depression which compositions are simultaneously administered to a patient in need thereof, wherein said first pharmaceutical composition is a composition comprising 5-20 mg vortioxetine or a pharmaceutically acceptable salt thereof for once daily oral administration and the second pharmaceutical composition is a composition comprising vortioxetine or a pharmaceutically acceptable salt thereof which together with said first composition achieves a steady-state plasma level of vortioxetine in said patient within 36 hours, such as within 24 or 18 or 12 hours from said simultaneous administration between 68 ng h/ml and 1625 ng h/ml, such as between 150 ng h/ml and 700 ng h/ml ($AUC_{0-24}$). In one embodiment, said first pharmaceutical composition comprises 5 mg vortioxetine or a pharmaceutically acceptable salt thereof and the steady-state vortioxetine plasma level is between 68 ng h/ml and 406 ng h/ml, such as between 150 ng h/ml and 170 ng h/ml, such as between 155 ng h/ml and 165 ng h/ml. In one embodiment, said first pharmaceutical composition comprises 10 mg vortioxetine or a pharmaceutically acceptable salt thereof and the steady-state vortioxetine plasma level is between 137 ng h/ml and 812 ng h/ml, such as between 145 ng h/ml and 315 ng g/ml, such as between 200 ng h/ml and 300 ng h/ml or between 300 ng h/ml and 340 ng h/ml, such as between 310 ng h/ml and 330 ng h/ml. In one embodiment, said first pharmaceutical composition comprises 15 mg vortioxetine or a pharmaceutically acceptable salt thereof and the steady-state vortioxetine plasma level is between 205 ng h/ml and 1219 ng h/ml, such as between 460 ng h/ml and 510 ng h/ml, such as between 470 ng h/ml and 500 ng h/ml. In one embodiment, said first pharmaceutical composition comprises 20 mg vortioxetine or a pharmaceutically acceptable salt thereof and the steady-state vortioxetine plasma level is between 273 ng h/ml and 1625 ng h/ml, such as between 600 ng h/ml and 700 ng h/ml, such as between 630 ng h/ml and 660 ng h/ml.

In one embodiment, the invention relates to the use of vortioxetine or a pharmaceutically acceptable salt thereof in the manufacture of a first pharmaceutical composition for once daily oral administration comprising 5-20 mg vortioxetine for the treatment of depression, wherein said first pharmaceutical composition is administered to a patient simultaneously with a second pharmaceutical composition which second pharmaceutical composition is a composition comprising vortioxetine or a pharmaceutically acceptable salts thereof which together with said first composition achieves a steady-state vortioxetine plasma level within 36 hours, such as with 24, 18 or 12 hours from said simultaneous administration in said patient between 68 ng h/ml and 1625 ng h/ml, such as between 150 ng h/ml and 700 ng h/ml ($AUC_{0-24}$). In one embodiment, said first pharmaceutical composition comprises 5 mg vortioxetine or a pharmaceutically acceptable salt thereof and the steady-state vortioxetine plasma level is between 68 ng h/ml and 406 ng h/ml, such as between 150 ng h/ml and 170 ng h/ml, such as between 155 ng h/ml and 165 ng h/ml. In one embodiment, said first pharmaceutical composition comprises 10 mg vortioxetine or a pharmaceutically acceptable salt thereof and the steady-state vortioxetine plasma level is between 137 ng h/ml and 812 ng h/ml, such as between 145 ng h/ml and 315 ng h/ml, such as between 200 ng h/ml and 300 ng h/ml or between 300 ng h/ml and 340 ng h/ml, such as between 310 ng h/ml and 330 ng h/ml. In one embodiment, said first pharmaceutical composition comprises 15 mg vortioxetine or a pharmaceutically acceptable salt thereof and the steady-state vortioxetine plasma level is between 205 ng h/ml and 1219 ng h/ml, such as between 460 ng h/ml and 510 ng h/ml, such as between 470 ng h/ml and 500 ng h/ml. In one embodiment, said first pharmaceutical composition comprises 20 mg vortioxetine or a pharmaceutically acceptable salt thereof and the steady-state vortioxetine plasma level is between 273 ng h/ml and 1625 ng h/ml, such as between 600 ng h/ml and 700 ng h/ml, such as between 630 ng h/ml and 660 ng h/ml.

In one embodiment, the invention relates to the use of vortioxetine or a pharmaceutically acceptable salt thereof in the manufacture of a pharmaceutical composition for the treatment of depression, wherein said pharmaceutical composition is administered to a patient simultaneously with a once daily oral pharmaceutical composition comprising 5-20 mg vortioxetine or a pharmaceutically acceptable salt thereof and wherein said simultaneous administration achieves a steady-state vortioxetine plasma level in said patient within 36 hours, such as within 24, 18 or 12 hours from said simultaneous administration between 68 ng h/ml and 1625 ng h/ml, such as between 150 ng h/ml and 700 ng h/ml ($AUC_{0-24}$). In one embodiment, said oral pharmaceutical composition comprises 5 mg vortioxetine or a pharmaceutically acceptable salt thereof and the steady-state vortioxetine plasma level is between 68 ng h/ml and 406 406 ng h/ml, such as between 150 ng h/ml and 170 ng h/ml, such as between 155 ng h/ml and 165 ng h/ml. In one embodiment, said oral pharmaceutical composition comprises 10 mg vortioxetine or a pharmaceutically acceptable salt thereof and the steady-state vortioxetine plasma level is between 137 ng h/ml and 812 ng h/ml, such as between 145 ng h/ml and 315 ng h/ml, such as between 200 ng h/ml and 300 ng h/ml or between 300 ng h/ml and 340 ng h/ml, such as between 310 ng h/ml and 330 ng h/ml. In one embodiment, said oral pharmaceutical composition comprises 15 mg vortioxetine or a pharmaceutically acceptable salt thereof and the steady-state vortioxetine plasma level is between 205 ng h/ml and 1219 ng h/ml, such as between 460 ng h/ml and 510 ng h/ml, such as between 470 ng h/ml and 500 ng h/ml. In one embodiment, said oral pharmaceutical composition comprises 20 mg vortioxetine or a pharmaceutically acceptable salt thereof and the steady-state vortioxetine plasma level is between 273 ng h/ml and 1625 ng h/ml, such as between 600 ng h/ml and 700 ng h/ml, such as between 630 ng h/ml and 660 ng h/ml.

As shown in Example 2, the simultaneous administration of 5 mg vortioxetine once daily per oral and a single dose of 8.5 mg vortioxetine intravenously administered over 1 hour achieves a steady-state vortioxetine plasma level which is similar to that achieved from an oral administration of 5 mg vortioxetine alone within 24 hours from said simultaneous administration. Similarly, the simultaneous administration of 10 mg vortioxetine once daily per oral and a single dose of 17 mg vortioxetine intravenously administered over 1 hour achieves a steady-state vortioxetine plasma level which is similar to that achieved from an oral administration of 10 mg vortioxetine alone within 24 hours from said simultaneous administration. Similarly, the simultaneous administration of 15 mg vortioxetine once daily per oral and a single dose of 25.5 mg vortioxetine intravenously administered over 1 hour achieves a steady-state vortioxetine plasma level which is similar to that achieved from an oral administration of 15 mg vortioxetine alone within 24 hours from said simultaneous administration. Similarly, the simultaneous administration of 20 mg vortioxetine once daily per oral and a single dose of 34 mg vortioxetine intravenously administered over 1 hour achieves a steady-state vortioxetine plasma level which is similar to that achieved from an oral administration of 20 mg vortioxetine alone within 24 hours from said simultaneous administration.

In one embodiment, the present invention provides a method for the treatment of depression, said method comprising the oral administration of 5 mg vortioxetine or a pharmaceutically acceptable salt thereof once daily and a single dose of 5 mg-12 mg, such as 6 mg-10 mg, such as 8.5 mg vortioxetine or a pharmaceutically acceptable salt thereof intravenously administered simultaneously with said oral administration to a patient in need thereof. In one embodiment, said single IV dose is administered over 15 minutes to 6 hours, such as 30 minutes to 3 hours, such as 1-2 hours. In particular, said IV dose is administered simultaneously with the first of said oral administrations. Alternatively, said IV dose is administered very quickly to the patients as an injection within a few seconds to a few minutes, such as up to 15 minutes.

In one embodiment, the present invention provides a method for the treatment of depression, said method comprising the oral administration of 10 mg vortioxetine or a pharmaceutically acceptable salt thereof once daily and a single dose of 14 mg-20 mg, such as 15 mg-19 mg, such as 17 mg vortioxetine or a pharmaceutically acceptable salt thereof intravenously administered simultaneously with said oral administration to a patient in need thereof. In one embodiment, said single IV dose is administered over 15 minutes to 6 hours, such as 30 minutes to 3 hours, such as 1-2 hours. In particular, said IV dose is administered simultaneously with the first of said oral administrations. Alternatively, said IV dose is administered very quickly to the patients as an injection within a few seconds to a few minutes, such as up to 15 minutes.

In one embodiment, the present invention provides a method for the treatment of depression, said method comprising the oral administration of 15 mg vortioxetine or a pharmaceutically acceptable salt thereof once daily and a single dose of 20 mg-30 mg, such as 22 mg-28 mg, such as 25.5 mg vortioxetine or a pharmaceutically acceptable salt thereof intravenously administered simultaneously with said oral administration to a patient in need thereof. In one embodiment, said single IV dose is administered over 15 minutes to 6 hours, such as 30 minutes to 3 hours, such as 1-2 hours. In particular, said IV dose is administered simultaneously with the first of said oral administrations. Alternatively, said IV dose is administered very quickly to the patients as an injection within a few seconds to a few minutes, such as up to 15 minutes.

In one embodiment, the present invention provides a method for the treatment of depression, said method comprising the oral administration of 20 mg vortioxetine or a pharmaceutically acceptable salt thereof once daily and a single dose of 30 mg-40 mg, such as 32 mg-36 mg, such as 34 mg vortioxetine or a pharmaceutically acceptable salt thereof intravenously administered simultaneously with said oral administration to a patient in need thereof. In one embodiment, said single IV dose is administered over 15 minutes to 6 hours, such as 30 minutes to 3 hours, such as 1-2 hours. In particular, said IV dose is administered simultaneously with the first of said oral administrations. Alternatively, said IV dose is administered very quickly to the patients as an injection within a few seconds to a few minutes, such as up to 15 minutes.

In one embodiment, the present invention provides an oral pharmaceutical composition for once daily administration comprising 5 mg vortioxetine or a pharmaceutically acceptable salt thereof for use in the treatment of depression wherein said oral pharmaceutical composition is for simultaneous administration with a single dose of 5 mg-12 mg, such as 6 mg-10 mg, such as 8.5 mg vortioxetine or a pharmaceutically acceptable salt thereof intravenously administered. In one embodiment, said single IV dose is administered over 15 minutes to 6 hours, such as 30 minutes to 3 hours, such as 1-2 hours. In particular, said IV dose is administered simultaneously with the first of said oral administrations. Alternatively, said IV dose is administered very quickly to the patients as an injection within a few seconds to a few minutes, such as up to 15 minutes.

In one embodiment, the present invention provides an oral pharmaceutical composition for once daily administration comprising 10 mg vortioxetine or a pharmaceutically acceptable salt thereof for use in the treatment of depression wherein said oral pharmaceutical composition is for simultaneous administration with a single dose of 14 mg-20 mg, such as 15 mg-19 mg, such as 17 mg vortioxetine or a pharmaceutically acceptable salt thereof intravenously administered. In one embodiment, said single IV dose is administered over 15 minutes to 6 hours, such as 30 minutes to 3 hours, such as 1-2 hours. In particular, said IV dose is administered simultaneously with the first of said oral administrations. Alternatively, said IV dose is administered very quickly to the patients as an injection within a few seconds to a few minutes, such as up to 15 minutes.

In one embodiment, the present invention provides an oral pharmaceutical composition for once daily administration comprising 15 mg vortioxetine or a pharmaceutically acceptable salt thereof for use in the treatment of depression wherein said oral pharmaceutical composition is for simultaneous administration with a single dose of 20 mg-30 mg, such as 22 mg-28 mg, such as 25.5 mg vortioxetine or a pharmaceutically acceptable salt thereof intravenously administered. In one embodiment, said single IV dose is administered over 15 minutes to 6 hours, such as 30 minutes to 3 hours, such as 1-2 hours. In particular, said IV dose is administered simultaneously with the first of said oral administrations. Alternatively, said IV dose is administered very quickly to the patients as an injection within a few seconds to a few minutes, such as up to 15 minutes.

In one embodiment, the present invention provides an oral pharmaceutical composition for once daily administration comprising 20 mg vortioxetine or a pharmaceutically acceptable salt thereof for use in the treatment of depression wherein said oral pharmaceutical composition is for simultaneous administration with a single dose of 30 mg-40 mg, such as 32 mg-36 mg, such as 34 mg vortioxetine or a pharmaceutically acceptable salt thereof intravenously administered. In one embodiment, said single IV dose is administered over 15 minutes to 6 hours, such as 30 minutes to 3 hours, such as 1-2 hours. In particular, said IV dose is administered simultaneously with the first of said oral administrations. Alternatively, said IV dose is administered very quickly to the patients as an injection within a few seconds to a few minutes, such as up to 15 minutes.

In one embodiment, the invention provides a pharmaceutical composition comprising 5 mg-12 mg, such as 6 mg-10 mg, such as 8.5 mg vortioxetine or a pharmaceutically acceptable salt for single intravenous administration wherein said pharmaceutical composition is for simultaneous administration with a once daily oral pharmaceutical composition comprising 5 mg vortioxetine or a pharmaceutically acceptable salt thereof. In one embodiment, said single IV dose is administered over 15 minutes to 6 hours, such as 30 minutes to 3 hours, such as 1-2 hours. In particular, said IV dose is administered simultaneously with the first of said oral administrations. Alternatively, said IV dose is administered very quickly to the patients as an injection within a few seconds to a few minutes, such as up to 15 minutes.

In one embodiment, the invention provides a pharmaceutical composition comprising 14 mg-20 mg, such as 15 mg-19 mg, such as 17 mg vortioxetine or a pharmaceutically acceptable salt for single intravenous administration wherein said pharmaceutical composition is for simultaneous administration with a once daily oral pharmaceutical composition comprising 10 mg vortioxetine or a pharmaceutically acceptable salt thereof. In one embodiment, said single IV dose is administered over 15 minutes to 6 hours, such as 30 minutes to 3 hours, such as 1-2 hours. In particular, said IV dose is administered simultaneously with the first of said oral administrations. Alternatively, said IV dose is administered very quickly to the patients as an injection within a few seconds to a few minutes, such as up to 15 minutes.

In one embodiment, the invention provides a pharmaceutical composition comprising 20 mg-30 mg, such as 22 mg-28 mg, such as 25.5 mg vortioxetine or a pharmaceutically acceptable salt for single intravenous administration wherein said pharmaceutical composition is for simultaneous administration with a once daily oral pharmaceutical composition comprising 15 mg vortioxetine or a pharmaceutically acceptable salt thereof. In one embodiment, said single IV dose is administered over 15 minutes to 6 hours, such as 30 minutes to 3 hours, such as 1-2 hours. In particular, said IV dose is administered simultaneously with the first of said oral administrations. Alternatively, said IV dose is administered very quickly to the patients as an injection within a few seconds to a few minutes, such as up to 15 minutes.

In one embodiment, the invention provides a pharmaceutical composition comprising 30 mg-40 mg, such as 32 mg-36 mg, such as 34 mg vortioxetine or a pharmaceutically acceptable salt for single intravenous administration wherein said pharmaceutical composition is for simultaneous administration with a once daily oral pharmaceutical composition comprising 20 mg vortioxetine or a pharmaceutically acceptable salt thereof. In one embodiment, said single IV dose is administered over 15 minutes to 6 hours, such as 30 minutes to 3 hours, such as 1-2 hours. In particular, said IV dose is administered simultaneously with the first of said oral administrations. Alternatively, said IV dose is administered very quickly to the patients as an injection within a few seconds to a few minutes, such as up to 15 minutes.

In one embodiment, the present invention provides an oral pharmaceutical composition for once daily administration comprising 5 mg vortioxetine or a pharmaceutically acceptable salt thereof and a single dose of 5 mg-12 mg, such as 6 mg-10 mg, such as 8.5 mg vortioxetine or a pharmaceutically acceptable salt thereof intravenously administered simultaneously with said oral administration for use in a method in the treatment of depression. In one embodiment, said single IV dose is administered over 15 minutes to 6 hours, such as 30 minutes to 3 hours, such as 1-2 hours. In particular, said IV dose is administered simultaneously with the first of said oral administrations. Alternatively, said IV dose is administered very quickly to the patients as an injection within a few seconds to a few minutes, such as up to 15 minutes.

In one embodiment, the present invention provides an oral pharmaceutical composition for once daily administration comprising 10 mg vortioxetine or a pharmaceutically acceptable salt thereof and a single dose of 14 mg-20 mg, such as 15 mg-19 mg, such as 17 mg vortioxetine or a pharmaceutically acceptable salt thereof intravenously administered simultaneously with said oral administration for use in a method for the treatment of depression. In one embodiment, said single IV dose is administered over 15 minutes to 6 hours, such as 30 minutes to 3 hours, such as 1-2 hours. In particular, said IV dose is administered simultaneously with the first of said oral administrations. Alternatively, said IV dose is administered very quickly to the patients as an injection within a few seconds to a few minutes, such as up to 15 minutes.

In one embodiment, the present invention provides an oral pharmaceutical composition for once daily administration comprising 15 mg vortioxetine or a pharmaceutically acceptable salt thereof and a single dose of 20 mg-30 mg, such as 22 mg-28 mg, such as 25.5 mg vortioxetine or a pharmaceutically acceptable salt thereof intravenously administered simultaneously with said oral administration for use in a method for the treatment of depression. In one embodiment, said single IV dose is administered over 15 minutes to 6 hours, such as 30 minutes to 3 hours, such as 1-2 hours. In particular, said IV dose is administered simultaneously with the first of said oral administrations. Alternatively, said IV dose is administered very quickly to the patients as an injection within a few seconds to a few minutes, such as up to 15 minutes.

In one embodiment, the present invention provides an oral pharmaceutical composition for once daily administration comprising 20 mg vortioxetine or a pharmaceutically acceptable salt thereof and a single dose of 30 mg-40 mg, such as 32 mg-36 mg, such as 34 mg vortioxetine or a pharmaceutically acceptable salt thereof intravenously administered simultaneously with said oral administration for use in a method for the treatment of depression. In one embodiment, said single IV dose is administered over 15 minutes to 6 hours, such as 30 minutes to 3 hours, such as 1-2 hours. In particular, said IV dose is administered simultaneously with the first of said oral administrations. Alternatively, said IV dose is administered very quickly to the patients as an injection within a few seconds to a few minutes, such as up to 15 minutes.

In one embodiment, the present invention provides the use of vortioxetine or a pharmaceutically acceptable salt thereof in the manufacture of an oral pharmaceutical composition for once daily administration comprising 5 mg vortioxetine for the treatment of depression, wherein said oral pharmaceutical composition is administered to a patient simultaneously with a single dose IV pharmaceutical composition comprising 5 mg-12 mg, such as 6 mg-10 mg, such as 8.5 mg vortioxetine or a pharmaceutically acceptable salt. In one embodiment, said single IV dose is administered over 15 minutes to 6 hours, such as 30 minutes to 3 hours, such as 1-2 hours. In particular, said IV dose is administered simultaneously with the first of said oral administrations. Alternatively, said IV dose is administered very quickly to the patients as an injection within a few seconds to a few minutes, such as up to 15 minutes.

In one embodiment, the present invention provides the use of vortioxetine or a pharmaceutically acceptable salt thereof in the manufacture of an oral pharmaceutical composition for once daily administration comprising 10 mg vortioxetine for the treatment of depression, wherein said oral pharmaceutical composition is administered to a patient simultaneously with a single dose IV pharmaceutical composition comprising 14 mg-20 mg, such as 15 mg-19 mg, such as 17 mg vortioxetine or a pharmaceutically acceptable salt. In one embodiment, said single IV dose is administered over 15 minutes to 6 hours, such as 30 minutes to 3 hours, such as 1-2 hours. In particular, said IV dose is administered simultaneously with the first of said oral administrations. Alternatively, said IV dose is administered very quickly to the patients as an injection within a few seconds to a few minutes, such as up to 15 minutes.

In one embodiment, the present invention provides the use of vortioxetine or a pharmaceutically acceptable salt thereof in the manufacture of an oral pharmaceutical composition for once daily administration comprising 15 mg vortioxetine for the treatment of depression, wherein said oral pharmaceutical composition is administered to a patient simultaneously with a single dose IV pharmaceutical composition comprising 20 mg-30 mg, such as 22 mg-28 mg, such as 25.5 mg vortioxetine or a pharmaceutically acceptable salt. In one embodiment, said single IV dose is administered over 15 minutes to 6 hours, such as 30 minutes to 3 hours, such as 1-2 hours. In particular, said IV dose is administered simultaneously with the first of said oral administrations. Alternatively, said IV dose is administered very quickly to the patients as an injection within a few seconds to a few minutes, such as up to 15 minutes.

In one embodiment, the present invention provides the use of vortioxetine or a pharmaceutically acceptable salt thereof in the manufacture of an oral pharmaceutical composition for once daily administration comprising 20 mg vortioxetine for the treatment of depression, wherein said oral pharmaceutical composition is administered to a patient simultaneously with a single dose IV pharmaceutical composition comprising 30 mg-40 mg, such as 32 mg-36 mg, such as 34 mg vortioxetine or a pharmaceutically acceptable salt. In one embodiment, said single IV dose is administered over 15 minutes to 6 hours, such as 30 minutes to 3 hours, such as 1-2 hours. In particular, said IV dose is administered simultaneously with the first of said oral administrations. Alternatively, said IV dose is administered very quickly to the patients as an injection within a few seconds to a few minutes, such as up to 15 minutes.

In one embodiment, the present invention provides the use of vortioxetine or a pharmaceutically acceptable salt thereof in the manufacture of a pharmaceutical composition for IV administration comprising 5 mg-12 mg, such as 6 mg-10 mg, such as 8.5 mg vortioxetine the treatment of depression, wherein said IV composition is administered simultaneously with an oral pharmaceutical composition for once daily administration comprising 5 mg vortioxetine or a pharmaceutically acceptable salt thereof for. In one embodiment, said single IV dose is administered over 15 minutes to 6 hours, such as 30 minutes to 3 hours, such as 1-2 hours. In particular, said IV dose is administered simultaneously with the first of said oral administrations. Alternatively, said IV dose is administered very quickly to the patients as an injection within a few seconds to a few minutes, such as up to 15 minutes.

In one embodiment, the present invention provides the use of vortioxetine or a pharmaceutically acceptable salt thereof in the manufacture of a pharmaceutical composition for IV administration comprising 14 mg-20 mg, such as 15 mg-19 mg, such as 17 mg vortioxetine for the treatment of depression, wherein said IV composition is administered simultaneously with an oral pharmaceutical composition for once daily administration comprising 10 mg vortioxetine or a pharmaceutically acceptable salt thereof. In one embodiment, said single IV dose is administered over 15 minutes to 6 hours, such as 30 minutes to 3 hours, such as 1-2 hours. In particular, said IV dose is administered simultaneously with the first of said oral administrations. Alternatively, said IV dose is administered very quickly to the patients as an injection within a few seconds to a few minutes, such as up to 15 minutes.

In one embodiment, the present invention provides the use of vortioxetine or a pharmaceutically acceptable salt thereof in the manufacture of a pharmaceutical composition for IV administration comprising 20 mg-30 mg, such as 22 mg-28 mg, such as 25.5 mg vortioxetine for the treatment of depression, wherein said IV composition is administered simultaneously with an oral pharmaceutical composition for once daily administration comprising 15 mg vortioxetine or a pharmaceutically acceptable salt thereof. In one embodiment, said single IV dose is administered over 15 minutes to 6 hours, such as 30 minutes to 3 hours, such as 1-2 hours. In particular, said IV dose is administered simultaneously with the first of said oral administrations. Alternatively, said IV dose is administered very quickly to the patients as an injection within a few seconds to a few minutes, such as up to 15 minutes.

In one embodiment, the present invention provides the use of vortioxetine or a pharmaceutically acceptable salt thereof in the manufacture of a pharmaceutical composition for IV administration comprising 30 mg-40 mg, such as 32 mg-36 mg, such as 34 mg vortioxetine for the treatment of depression, wherein said IV composition is administered simultaneously with an oral pharmaceutical composition for once daily administration comprising 20 mg vortioxetine or a pharmaceutically acceptable salt thereof. In one embodiment, said single IV dose is administered over 15 minutes to 6 hours, such as 30 minutes to 3 hours, such as 1-2 hours. In particular, said IV dose is administered simultaneously with the first of said oral administrations. Alternatively, said IV dose is administered very quickly to the patients as an injection within a few seconds to a few minutes, such as up to 15 minutes.

In one embodiment, the present invention provides a kit comprising an oral pharmaceutical composition for once daily administration comprising 5 mg-20 mg vortioxetine or a pharmaceutical acceptable salt thereof and a pharmaceutical composition for IV administration comprising 5 mg-40 mg vortioxetine or a pharmaceutically acceptable salt thereof.

In one embodiment, the present invention provides a kit comprising an oral pharmaceutical composition for once daily administration comprising 5 mg vortioxetine or a pharmaceutical acceptable salt thereof and a pharmaceutical composition for IV administration comprising 5 mg-12 mg, such as 6 mg-10 mg, such as 8.5 mg vortioxetine or a pharmaceutically acceptable salt thereof.

In one embodiment, the present invention provides a kit comprising an oral pharmaceutical composition for once daily administration comprising 10 mg vortioxetine or a pharmaceutical acceptable salt thereof and a pharmaceutical composition for IV administration comprising 14 mg-20 mg, such as 15 mg-19 mg, such as 17 mg vortioxetine or a pharmaceutically acceptable salt thereof.

In one embodiment, the present invention provides a kit comprising an oral pharmaceutical composition for once daily administration comprising 15 mg vortioxetine or a pharmaceutical acceptable salt thereof and a pharmaceutical composition for IV administration comprising 20 mg-30 mg, such as 22 mg-28 mg, such as 25.5 mg vortioxetine or a pharmaceutically acceptable salt thereof.

In one embodiment, the present invention provides a kit comprising an oral pharmaceutical composition for once daily administration comprising 20 mg vortioxetine or a pharmaceutical acceptable salt thereof and a pharmaceutical composition for IV administration comprising 30 mg-40 mg, such as 32 mg-36 mg, such as 34 mg vortioxetine or a pharmaceutically acceptable salt thereof.

As alternatives to IV administration as discussed above other administration forms including nasal, buccal, sublingual and rectal administration may be used. Such administrations forms avoid absorption through the intestines and first-pass metabolism and are as such likely to result in a rapid increase in vortioxetine level in the plasma. It is an advantage if the bioavailability of vortioxetine as formulated for nasal, buccal, sublingual or rectal administration is high to avoid the need of having to administer large amounts of vortioxetine to achieve the desired effect. Preferably, the bioavailability (as compared to IV administration) is above 70%, such as above 80%, such as above 90%. The doses for nasal, buccal, sublingual or rectal administration (relative to the IV doses discussed above) may be adjusted according to the actual bioavailability of the administration form used.

After administration via a nasal, buccal, sublingual or rectal route, vortioxetine is absorbed across mucosa in the nose, mouth or rectum. The bioavailability of a compound across mucosa may be controlled by the pharmaceutical composition in which the compound is presented. For example, the use of muco-adhesive ingredients may prolong the contact time between the compound and the mucosa and thereby increase bioavailability. Examples of muco-adhesives include polymers, such as carbomers, chitosans, cellulose and starch derivatives. Absorption enhancing ingredients may also be used to reversibly modify the barrier properties of the relevant epithelium to increase bioavailability. Examples of absorption enhancers include surfactants, bile salts and fatty acids, such as oleic acid [*Curr Probl Dermatol*, 40, 20-35, 2011; *Clin Pharmacokinet*, 42, 1107-1128, 2003].

The present invention relates to the use of an oral pharmaceutical composition comprising vortioxetine or a pharmaceutically acceptable salt thereof administered simultaneously with a second pharmaceutical composition comprising vortioxetine or a pharmaceutically acceptable salt thereof to quickly achieve steady-state vortioxetine plasma level similar to that obtained from the administration of said oral composition alone. Both pharmaceutical compositions of the present invention may, in addition to the active ingredient, contain a pharmaceutically acceptable carrier.

Preparation of pharmaceutical compositions and extensive lists of carriers used in pharmaceutical compositions may be found e.g. in Remington, The Science and Practice of Pharmacy, $22^{th}$ Ed., Pharmaceutical Press, 2013.

Pharmaceutical compositions for oral administration include solid dosage forms such as capsules, tablets, dragees, pills, lozenges, powders and granules. Where appropriate, they can be prepared with coatings. Suitable carriers for oral compositions include lactose, mannitol, microcrystalline cellulose, hydroxypropyl cellulose, sodium starch glycolate, corn starch, potato starch, terra alba, sucrose, cyclodextrin, talc, gelatine, agar, pectin, acacia, magnesium stearate, stearic acid and lower alkyl ethers of cellulose.

Tablets may be prepared by mixing vortioxetine or a pharmaceutically acceptable salt thereof with ordinary carriers followed by the compression of the mixture in a conventional tabletting machine. Any other adjuvants or additives usually used for such purposes such as colourings, preservation etc. may be used provided that they are compatible with the active ingredients.

Vortioxetine is available in a commercial oral pharmaceutical composition comprising 5 mg, 10 mg, 15 mg or 20 mg vortioxetine HBr and mannitol, microcrystalline cellulose, hydroxypropyl cellulose, sodium starch glycolate, magnesium stearate with a film coating which consists of hypromellose, titanium dioxide, polyethylene glycol 400, iron oxide red (5 mg, 15 mg, and 20 mg) and iron oxide yellow (10 mg and 15 mg).

A pharmaceutical composition for intravenous administration as used in the present invention may be an aqueous solution comprising vortioxetine or a pharmaceutically acceptable salt thereof. Such intravenous composition may additionally comprise solvents, buffers, surfactant, tonicity agent, preservatives and antioxidants. Examples of solvents include ethanol, propylene glycol, glycerol and polyethylene glycol. The solubility of vortioxetine or a pharmaceutically acceptable salt thereof may be enhanced by the addition of a e.g. a co-solvent or cyclodextrin or a derivative thereof. Examples of surfactants include tweens, spans and mono- and diglycerides. Examples of tonicity agents include dextrose, glycerine and sodium chloride. Examples of preservatives include ethanol, benzoic acid, sorbic acid, methylparaben, propylparaben and benzylalcohol. Examples of antioxidants include propyl gallate, ascorbic acid and EDTA. It is important that a pharmaceutical composition for intravenous administration is sterile. Such composition may either be packaged ready-to-use or as a high-concentration composition which is mixed with e.g. isotonic saline prior to, or as part of, the intravenous infusion.

An example of a pharmaceutical composition for intravenous administration is provided below:

| | |
|---|---|
| Vortioxetine HBr | 1.271 mg |
| Sulfobutyl Ether β-cyclodextrin Sodium | 16 mg |
| Sodium Chloride | 9 mg |
| Water | add 1 ml. |

A suitable volume of this composition may be mixed with isotonic saline (e.g., 50-500 ml) for intravenous administration.

A pharmaceutical composition for nasal administration where the active ingredient is absorbed via the nasal mucosa is typically an aqueous solution, emulsion or suspension administered to the nasal cavity in drops or in sprays. A nasal composition is typically formulated to be similar to nasal secretion with respect to tonicity, pH and viscosity to maintain normal ciliary action. A pharmaceutical composition for nasal administration may contain buffers, NaCl or methylcellulose and preservatives. Pharmaceutical compositions for nasal administration are normally packaged in dropper or spray bottles.

A pharmaceutical composition comprising vortioxetine or a pharmaceutically acceptable salt thereof for buccal including sublingual administration preferable disintegrate rapidly when inserted into the buccal pouch or placed under the tongue. The disintegration time upon insertion into the mouth can normally be extrapolated from the time to disintegrate in water at 37° C., e.g., as described in Remington, The Science and Practice of Pharmacy, 22$^{th}$ Ed., Pharmaceutical Press, 2013 page 968. In the present context, rapid disintegration is intended to indicate disintegration in water at 37° C. as described above within 60 seconds, such as within 30 seconds, such as within 10 seconds.

A pharmaceutical composition for buccal or sublingual administration may comprise a water soluble or water dispersible carrier, such as polysaccharides like hydrolysed dextran, dextrin, mannitol, and alginates, or mixtures thereof with other carrier materials like polyvinyl alcohol, polyvinylpyrrolidine and water-soluble cellulose derivatives, like hydroxypropyl cellulose.

A pharmaceutical composition comprising vortioxetine or a pharmaceutically acceptable salt thereof for rectal administration may be in the form of suppositories, microclysms, soft gelatin rectal capsules, rectal ointments, sprays and the like. For this purpose, conventional carriers and techniques can be used. As an example, for the formulation of soft gelatin capsules, an oily dispersion of vortioxetine or a pharmaceutically acceptable salt thereof can be used, obtained using carriers such as polyethylene glycols, vaseline oil, vegetable and semisynthetic officinal oils including medium chain saturated triglycerides. In order to avoid settling of the ingredients dispersants such as polyalcohol fatty acid esters, polyoxyethylene fatty acid esters, polyoxyethylene fatty alcohol esters and, polyoxyethylene sorbitane ester derivatives may be applied.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various compounds of the invention or particular described aspect, unless otherwise indicated.

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

EXAMPLES

Example 1 PET Monkey Study

Positron Emission Tomography (PET) was used to assess changes in the endogenous serotonin concentration in living rhesus monkeys. The objective of the present study was two-fold. A first PET study was designed to determine the dose response relation for vortioxetine- and citalopram-induced serotonin transporter occupancy in the monkey brain using the SERT radio-ligand [$^{11}$C]MADAM. The chemical name for [$^{11}$C]MADAM is [$^{11}$C] N,N-dimethyl-2-(2-amino-4-methylphenylthio)benzylamine. A second PET study was designed to compare the release capacity of vortioxetine and citalopram after doses that induce similar SERT occupancy using the 5-HT$_{1B}$ receptor radio-ligand [$^{11}$C]AZ10419369.

FIG. 1 illustrates the study design used for assessment of serotonin releasing capacities. A similar study design was applied for assessment of SERT occupancy.

The SERT occupancy study showed that 0.3 mg/kg and 1.0 mg/kg vortioxetine intravenously administered corresponds to approximately 50% and 80% SERT occupancy, respectively. These occupancy levels corresponds to clinically relevant occupancy levels as measured in PET studies in healthy subjects [*Basic Clin Pharmacol Tox,* 110, 401-404, 2012]. Similarly, the 0.3 mg/kg citalopram intravenously administered corresponds to a SERT occupancy of approximately 83%, which is also known to be clinically relevant [Am J Psych 158, 1843-1849, 2001].

The table below sets out the changes in [$^{11}$C] AZ10419369-5-HT$_{1B}$ receptor binding potential (BP$_{ND}$) in various brain regions after vortioxetine and citalopram administration. The results are shown as mean±standard error for n=3, and * indicates p<0.05 by two-tailed Paired t-test.

| Brain region | ΔBP$_{ND}$ (% of baseline) | | |
|---|---|---|---|
| | Vortioxetine 1.0 mg/kg | Vortioxetine 0.3 mg/kg | Citalopram 0.3 mg/kg |
| Putamen | −40.8 ± 7.9* | −15.6 ± 8.5 | 7.3 ± 12.0 |
| Caudate nucleus | −47.0 ± 8.0* | −23.2 ± 7.4 | 7.1 ± 7.5 |
| Ventral striatum | −47.7 ± 8.5* | −25.6 ± 5.4* | 3.1 ± 10.8 |
| Globus pallidus | −41.2 ± 6.4* | −16.3 ± 5.1 | −1.6 ± 9.6 |
| Amygdala | −39.5 ± 11.5* | −12.4 ± 10.5 | 4.6 ± 11.6 |
| Hippocampus | −27.0 ± 6.8* | −9.4 ± 8.9 | 5.4 ± 12.5 |
| Frontal gyrus | −32.8 ± 9.5* | −8.2 ± 8.2 | 12.4 ± 9.3 |
| Occipital gyrup | −54.1 ± 4.2* | −24.3 ± 3.2* | 15.7 ± 11.1 |
| Thalamus | −42.5 ± 7.0* | −23.9 ± 5.0* | 0.3 ± 5.6 |
| Midbrain | −49.4 ± 7.1* | −21.9 ± 3.0* | 2.7 ± 5.3 |
| Dorsal raphe nucleus | −55.0 ± 3.3* | −28.3 ± 13.6 | −21.2 ± 5.7* |

Example 2 Simulation of Plasma Profiles

A population pharmacokinetic (popPK) model describing the disposition of vortioxetine is available in the literature together with the exposure levels ($C_{max}$ and AUC) at steady-state after oral administration [Basic Clin Pharmacol Tox, 115, 552-559, 2014]. The bioavailability of vortioxetine after oral administration is 75% relative to IV administration [Basic Clin Pharmacol Toxicol 111, 198-205, 2012]. The popPK model together with the oral bioavailability of vortioxetine was used to calculate which dose of a single IV administered vortioxetine infused over 1 hour is necessary to simultaneously administer with once daily orally administered vortioxetine in order to obtain an exposure level within 24 hours corresponding to the steady-state plasma level that would have been obtained from the oral administration alone. The table below shows the results.

| Orally administered dose (mg vortioxetine) | IV dose necessary in order to achieve steady-state vortioxetine plasma level corresponding to orally administered dose within 24 hours (mg vortioxetine) |
|---|---|
| 5 | 8.5 |
| 10 | 17 |
| 15 | 25.5 |
| 20 | 34 |

Example 3 Clinical Trial

The clinical effect of simultaneous administration of oral vortioxetine and IV vortioxetine may be assessed in a clinical study as shown here.

In a double-blind study, patients are randomised (1:1) to either of two dose regimes. (1) Vortioxetine 17 mg IV and vortioxetine 10 mg/day (tablet), or (2) placebo IV and vortioxetine 10 mg/day (tablet). Patients enrolled in the study have recurrent major depressive disorder diagnosed according to DSM-V.

On day 0 patients have 17 mg vortioxetine or placebo IV infused over 2 hours. From day 0 to day 14 all patients receive 10 mg/day vortioxetine orally.

Efficacy of the two dose regimes is assessed by the MADRS scale throughout the study.

In particular, a total of 55 patients (27 and 28 in each treatment group) were recruited to an interventional, prospective, multi-national, multi-site, randomised, double-blind, parallel-group, fixed-dose study. The patients were outpatients with a primary diagnosis of recurrent major depressive disorder according to DSM-5™ criteria (classification code 296.3x), who had a Montgomery Asberg Depression Rating Scale (MADRS) total score ≥30 at the Screening Visit and at the Baseline Visit, were ≥18 and ≤65 years of age, had had the current major depressive episode for ≥3 months and was an outpatient at a psychiatric setting willing to be hospitalised for 24 hours following the Baseline Visit.

The study consisted of a Screening Period—2 to 14-day period from screening to randomisation, a Treatment Period—15-day double-blind treatment period with one initial IV administration of 17 mg vortioxetine or saline and daily oral treatment with vortioxetine 10 mg and a Safety Follow-up Period—4-week period after end of treatment or after withdrawal from the study.

At the Baseline Visit, patients were equally randomised (1:1) to either of the following two dose regimens: vortioxetine 17 mg single dose (IV) and vortioxetine 10 mg/day (tablet) or placebo single dose (IV) and vortioxetine 10 mg/day (tablet).

Patients randomised to the vortioxetine IV dose regimen, received a single double-blind IV dose of 17 mg vortioxetine, infused over 2 hours, on Day 0 (baseline). Patients randomised to the vortioxetine oral dose regimen received a single double-blind IV dose of placebo (saline), infused over 2 hours, on Day 0. From Day 0 to Day 14, all patients in both treatment groups also received open labelled 10 mg/day vortioxetine by oral administration (tablets).

Following the IV infusion, patients stayed hospitalised for approximately 24 hours for close observation. After the hospitalisation period, patients continued the study on an outpatient basis.

Efficacy and safety data were collected at Days 0, 1, 3, 7, and 14, including MADRS and clinical global impression (CCI).

As expected, the outcome difference between the two treatment groups became smaller over time as the effect of the active IV dose two weeks earlier levelled off. Table 1 below shows the MADRS readout at day 0 to 7. The results show a marked decrease in MADRS scores (i.e. an improvement of the clinical sign of depression) and a faster decrease in the vortioxetine IV arm.

TABLE 1

| Change in MADRS total score day 1-7 | | | | | |
|---|---|---|---|---|---|
| Treatment group | N | Mean (Baseline) | Day | Mean | Difference |
| PBO IV + VOR oral | 28 | 33.4 | 1 | −5.5 | |
| | | | 3 | −10.3 | |
| | | | 7 | −13.4 | |
| VOR IV + VOR oral | 27 | 34.6 | 1 | −6.9 | −1.4 |
| | | | 3 | −12.1 | −1.7 |
| | | | 7 | −13.7 | −0.3 |

The full MADRS scale may not be a suitable tool for gauging the early onset of anti-depressant effect of a drug because some of the ten items addressed in the MADRS test may require longer assessment time to validly assess a given symptom. For example, the MADRS item "Concentration Difficulties" requires that the patient has been exposed to a situation during the treatment where a change in the ability to concentrate could be identified in order for that item to truly reflect a treatment effect. It has recently been suggested (2017 ASCP Annual Meeting (Miami Beach, Fla., May 29-Jun. 2, 2017)) that the MADRS items "Apparent sadness", "Reported sadness", Inner tension", "Pessimistic thoughts" and "Suicidal thoughts" may be a better suited sub-set of the MADRS scale to gauge the short-term effects of an antidepressant. Table 2 below shows the effect in the two treatment arms as measured by this 5-item MADRS scale.

TABLE 2

Change in 5-item MADRS score day 1-14

| Treatment group | N | Mean (Baseline) | Day | Mean | Difference |
|---|---|---|---|---|---|
| PBO IV + VOR oral | 28 | 15.71 | 1 | −3.92 | |
| | | | 3 | −6.00 | |
| | | | 7 | −7.03 | |
| | | | 14 | 9.21 | |
| VOR IV + VOR oral | 27 | 34.6 | 1 | −5.05 | −1.13 |
| | | | 3 | −6.96 | −0.96 |
| | | | 7 | −8.30 | −1.27 |
| | | | 14 | 9.37 | −0.16 |

Moreover, Table 3 below depicts the response rate in the two arms, i.e. the fraction of the patients experiencing a more than or equal to 50% reduction on the MADRS scale. The data clearly shows a markedly larger proportion of the patients responding to the vortioxetine IV treatment early in the study and that the difference between the two arms disappears over time.

TABLE 3

% responders (≥50% reduction on MADRS Scale)

| Day | PBO IV + VOR oral | VOR IV + VOR oral |
|---|---|---|
| 1 | 0 | 3.7 |
| 3 | 14.3 | 29.6 |
| 7 | 28.6 | 40.7 |
| 14 | 50.0 | 48.1 |

Table 4 below depicts the response rate as measured by the fraction of the patients with an improvement on the CGI-I scale of 2 or more. Again, the data shows a markedly faster response to the vortioxetine IV treatment, and assessed this way the vortioxetine IV treatment arm is superior also at day 14.

TABLE 4

% responders (CGI-I ≤ 2)

| Day | PBO IV +VOR oral | VOR IV +VOR oral |
|---|---|---|
| 1 | 7.1 | 18.5 |
| 3 | 39.3 | 50.0 |
| 7 | 42.9 | 53.8 |
| 14 | 67.9 | 73.1 |

Finally, Table 5 below shows the vortioxetine plasma levels sampled during the first 24 hours post-dose and at study end. The popPK model from example 2 was used to simulate vortioxetine plasma levels based on the observed data from Table 5. This simulation shows that $AUC_{0-24}$ at day 0 for the VOR IV+VOR oral treated patients was 251±46 ng h/ml and 47±20 ng h/ml for the PBO IV+VOR oral treated patients. The simulation also shows that $AUC_{0-24}$ at day 14 for the PBO IV+VOR oral treated patients is 230±85 ng h/ml. That is, the steady-state plasma level of vortioxetine achieved from the combined IV and oral vortioxetine administration the within 24 hours from the first dosing is essentially the same as the steady-state vortioxetine plasma level achieved at day 14 following the administration of once-daily oral vortioxetine alone in that period.

TABLE 5

Vortioxetine plasma levels (ng/ml)

| Visit | PBO IV + VOR oral | VOR IV + VOR oral |
|---|---|---|
| Day 0, 2 hours | 0.56 ± 1.18 | 11.1 ± 9.3 |
| Day 0, 8 hours | 2.8 ± 1.8 | 11.0 ± 2.9 |
| Day 0, 24 hours | 2.6 ± 1.3 | 8.6 ± 2.6 |
| Day 14 | 9.9 ± 5.3 | 10.8 ± 7.0 |

Overall, the data strongly indicate that patients receiving a single dose IV vortioxetine in combination with oral vortioxetine experience a faster on-set of anti-depressive action than patients receiving placebo IV and oral vortioxetine.

The invention claimed is:

1. A method for the treatment of depression, said method comprising:
   simultaneously administering two pharmaceutical compositions to a patient in need thereof,
   wherein the first pharmaceutical composition is a composition comprising vortioxetine or a pharmaceutically acceptable salt thereof for once daily oral administration, and the second pharmaceutical composition is a composition comprising vortioxetine or a pharmaceutically acceptable salt thereof which, together with said first composition, achieves a steady-state plasma level of vortioxetine in said patient within 36 hours from said simultaneous administration, which steady-state plasma level is essentially the same as the steady-state vortioxetine plasma level achieved by the administration to said patient of said first composition alone; and
   wherein said second pharmaceutical composition is administered nasally.

2. The method of claim 1, wherein said first pharmaceutical composition comprises 5 mg-20 mg vortioxetine or a pharmaceutically acceptable salt thereof, and the second pharmaceutical composition is a composition comprising vortioxetine or a pharmaceutically acceptable salt thereof which, together with said first composition, achieves a steady-state plasma level between 68 ng h/ml and 1625 ng h/ml vortioxetine in said patient within 24 hours from said simultaneous administration.

3. The method of claim 1, wherein said first pharmaceutical composition comprises 5 mg-20 mg vortioxetine or a pharmaceutically acceptable salt thereof and said second pharmaceutical composition comprises 7 mg-57 mg vortioxetine or a pharmaceutically acceptable salt thereof for nasal administration to achieve a steady-state plasma level of vortioxetine between 68 ng h/ml and 1625 ng h/ml vortioxetine in said patient within 24 hours from said simultaneous administration.

4. The method of claim 1, comprising simultaneously administering 10 mg vortioxetine or a pharmaceutically acceptable salt thereof once daily through oral administration and a single dose of 14 mg-29 mg vortioxetine nasally administered with the oral administration.

5. The method of claim 1, wherein the first pharmaceutical composition is in the form of a capsules, a tablet, a dragee, a pill, a lozenge, a powder, or granules.

6. A kit, comprising:
- an oral pharmaceutical composition comprising 5 mg-20 mg vortioxetine or a pharmaceutical acceptable salt thereof for once daily oral administration; and
- a second pharmaceutical composition for nasal administration comprising 7 mg-57 mg vortioxetine or a pharmaceutically acceptable salt thereof.

7. The kit of claim 6, wherein the oral pharmaceutical composition comprises 10 mg vortioxetine or a pharmaceutical acceptable salt thereof.

8. The kit of claim 6, wherein the oral pharmaceutical composition is in the form of a capsules, a tablet, a dragee, a pill, a lozenge, a powder, or granules.

9. The kit of claim 6, wherein the second pharmaceutical composition comprises 14-29 mg vortioxetine or a pharmaceutically acceptable salt thereof.

\* \* \* \* \*